United States Patent
Kari et al.

[11] Patent Number: 6,126,007
[45] Date of Patent: Oct. 3, 2000

[54] TISSUE VALVE HOLDER

[75] Inventors: Erik E. Kari, Albertville; Richard F. Schroeder, Oakdale, both of Minn.; Jason Kalgreen, Palo Alto, Calif.

[73] Assignee: St. Jude Medical, Inc., St. Paul, Minn.

[21] Appl. No.: 09/223,442

[22] Filed: Dec. 30, 1998

[51] Int. Cl.⁷ ..................................................... A61B 17/06
[52] U.S. Cl. ........................... 206/438; 206/363; 206/583
[58] Field of Search ..................... 206/363, 438, 206/525, 583; 623/2, 900

[56] References Cited

U.S. PATENT DOCUMENTS

| | | |
|---|---|---|
| 3,409,013 | 11/1968 | Berry . |
| 3,623,212 | 11/1971 | Child . |
| 3,628,535 | 12/1971 | Ostrowsky et al. . |
| 3,710,744 | 1/1973 | Goodenough et al. . |
| 3,828,787 | 8/1974 | Anderson et al. . |
| 3,839,741 | 10/1974 | Haller . |
| 3,997,923 | 12/1976 | Possis . |
| 4,182,446 | 1/1980 | Penny . |
| 4,185,636 | 1/1980 | Gabbay et al. . |
| 4,211,325 | 7/1980 | Wright . |
| 4,506,394 | 3/1985 | Bedard . |
| 4,585,453 | 4/1986 | Martin et al. . |
| 4,655,218 | 4/1987 | Kulik et al. . |
| 4,679,556 | 7/1987 | Lubock et al. . |
| 4,683,883 | 8/1987 | Martin . |
| 4,702,250 | 10/1987 | Ovil et al. . |
| 4,801,015 | 1/1989 | Lubock et al. . |
| 4,865,600 | 9/1989 | Carpentier et al. . |
| 4,932,965 | 6/1990 | Phillips . |
| 5,089,015 | 2/1992 | Ross . |
| 5,163,955 | 11/1992 | Love et al. . |
| 5,197,979 | 3/1993 | Quintero et al. . |
| 5,236,450 | 8/1993 | Scott . |
| 5,290,300 | 3/1994 | Cosgrove et al. . |
| 5,336,258 | 8/1994 | Quintero et al. . |
| 5,476,510 | 12/1995 | Eberhardt et al. . |
| 5,480,425 | 1/1996 | Ogilive . |
| 5,489,297 | 2/1996 | Duran . |
| 5,531,785 | 7/1996 | Love et al. . |
| 5,560,487 | 10/1996 | Starr . |
| 5,681,740 | 10/1997 | Messier et al. ........................... 206/438 |
| 5,697,382 | 12/1997 | Love et al. . |
| 5,716,401 | 2/1998 | Eberhardt et al. . |
| 5,720,391 | 2/1998 | Dohm et al. . |
| 5,823,342 | 10/1998 | Caudillo et al. ........................... 206/438 |
| 5,843,177 | 12/1998 | Vanney et al. ................................ 623/2 |
| 5,868,253 | 2/1999 | Krueger et al. ........................... 206/438 |

*Primary Examiner*—Paul T. Sewell
*Assistant Examiner*—Luan K. Bui
*Attorney, Agent, or Firm*—Hallie A. Finucane, Esq.; Westman, Champlin & Kelly, P.A.

[57] ABSTRACT

A tissue valve holder for holding a tissue heart valve bioprosthesis such that the tissue valve may be supported without contacting any surface, regardless of whether or not the valve is in a container. The tissue valve holder includes a holder assembly adapted to be secured to the tissue valve. The holder assembly may include a holder body and a removable disk. The holder assembly and the tissue valve secured thereto rest on a support structure. The support structure may comprise a support surface and a plurality of support legs. The support surface, in turn, may comprise an annular ring with the support legs connected thereto. The holder assembly rests on the support surface with the tissue valve suspended in the center of the ring.

11 Claims, 7 Drawing Sheets

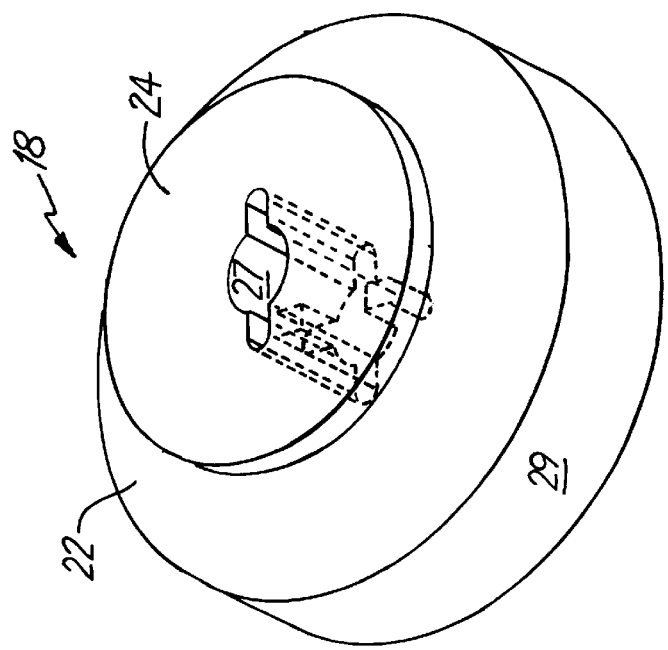
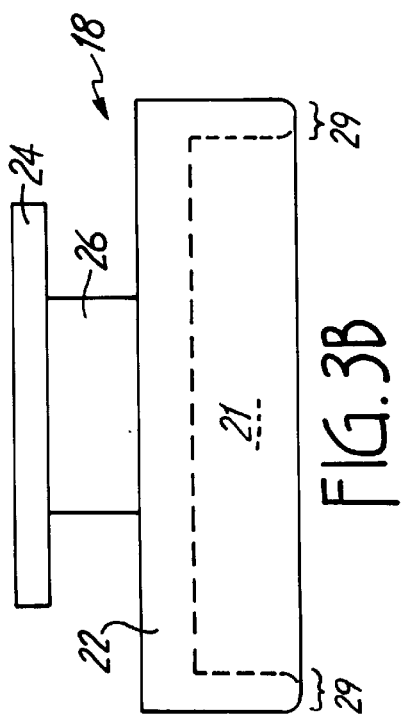
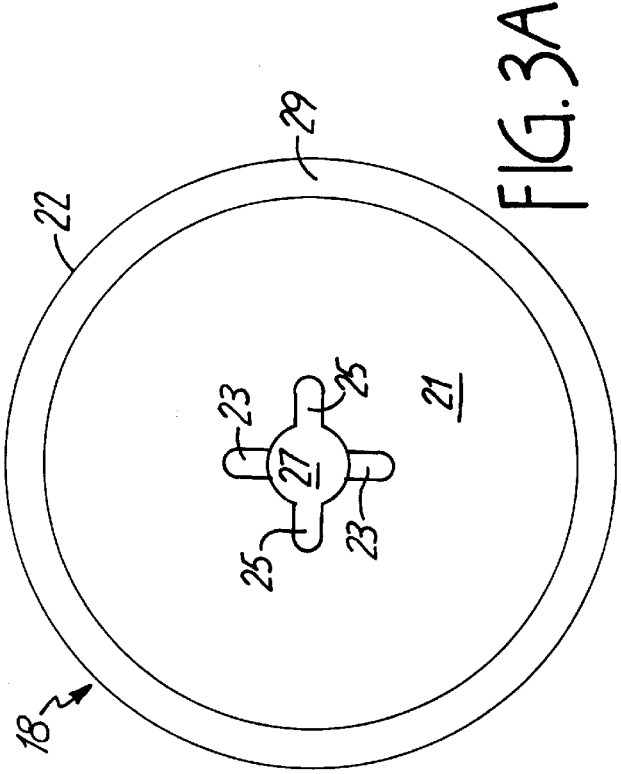

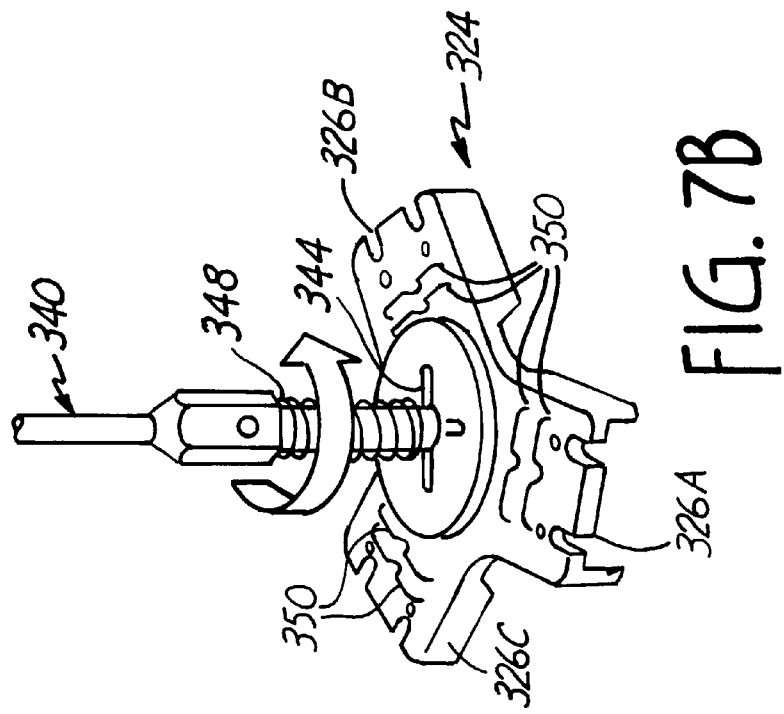
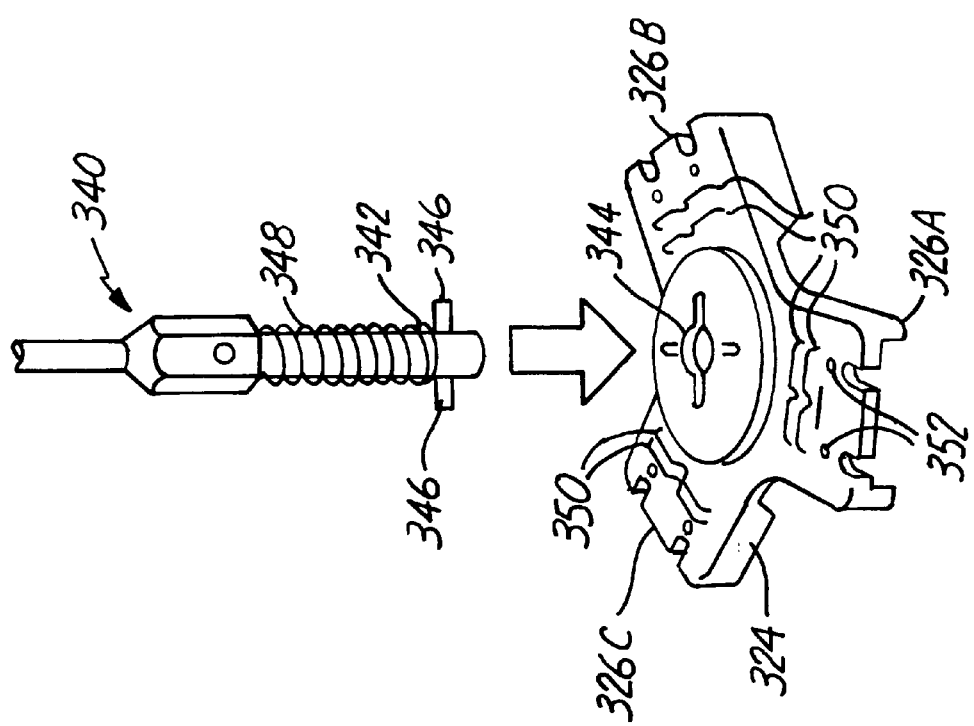

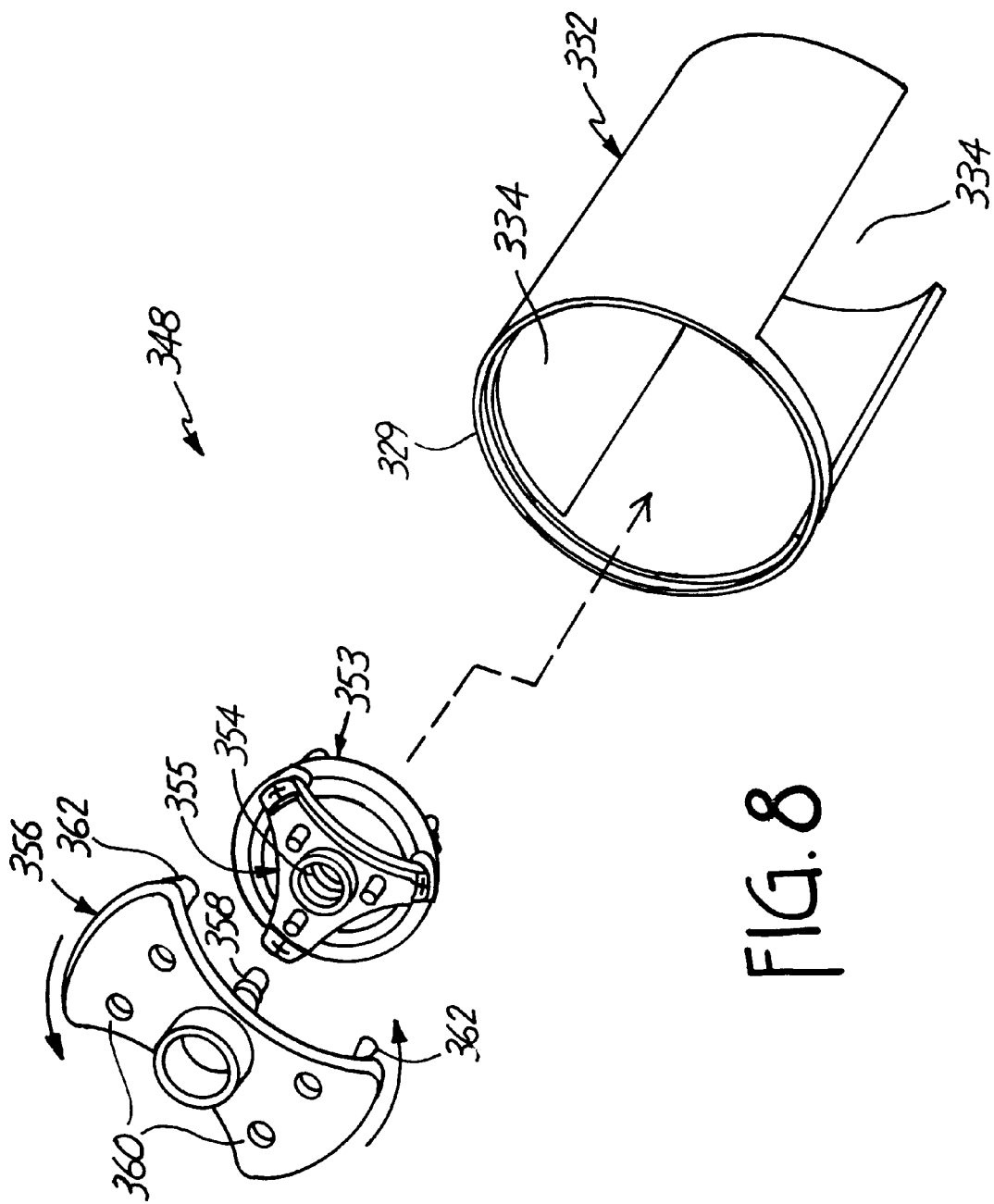

TISSUE VALVE HOLDER

FIELD OF THE INVENTION

The present invention generally relates to tissue heart valve bioprostheses. More specifically, the present invention relates to holders for tissue heart valve bioprostheses.

BACKGROUND OF THE INVENTION

Prosthetic valves are utilized to replace malformed, damaged, diseased or otherwise malfunctioning valves in body passageways, such as heart valves including the tricuspid valve, mitral valves the aortic valve and the pulmonary valve. Such prosthetic heart valves are typically implanted into the heart either by open chest surgery, which requires a sternotomy, or by minimally invasive surgery, which requires a thoracotomy between adjacent ribs.

Heart valve prosthesis may be divided into two groups, namely tissue valves and mechanical valves. Typically, bioprosthetic tissue valves are harvested from a suitable animal, usually a porcine heart, prepared according to known methods, and may be mounted to a stent to facilitate implantation. Tissue valves prepared from pericardial tissue are also known in the art. Mechanical valves, by contrast, utilize synthetic materials to form a valve having a ball, a disk, a pair of leaflets (bileaflet), or a plurality of leaflets to regulate blood flow therethrough.

A number of packaging designs have been developed for holding and transporting tissue heart valve bioprostheses. One such design provides a tissue valve holder which suspends the tissue valve in a container having a storage solution. The tissue valve remains suspended in the solution and sealed within the container until the valve is removed by the surgeon for implantation into a patient.

An example of such a packaging design is disclosed in U.S. Pat. No. 5,560,487 to Starr. The packaging system disclosed in Starr utilizes a holder that suspends the tissue valve in a container of preservative. However, the holder is not able to suspend the tissue valve once removed from the container. In the case of a valved conduit, the holder disclosed in Starr does not maintain the shape of the tissue valve because only three points of contact are used to secure the aortic root of the valve to the holder.

Maintaining the tissue valve in suspension after removal from the container is desirable to prevent the valve from coming into contact with other surfaces which may not be sterile. Maintaining the shape of the valve in the container is desirable to avoid deforming or damaging the valve during shipping and handling. As such, an improved holder for holding a tissue valve is desirable.

SUMMARY OF THE INVENTION

The present invention provides an improved tissue valve holder for holding a tissue heart valve bioprosthesis such that the valve may be supported without contacting any surface, whether or not the valve is in a container, by utilizing a separate support structure. In addition, in one aspect, the present invention provides an improved tissue valve holder that maintains the shape of the valved conduit while packaged by utilizing a continuous contact interface between the holder and the aortic root of the valve.

The tissue valve holder of the present invention includes a holder assembly adapted to be secured in the conduit outflow of the tissue valve using a securing member surrounding the conduit outflow. The holder assembly may include a holder body and a removable disk. The holder assembly and the tissue valve secured thereto rest on a support structure that includes a plurality of support legs and a support surface. The support surface may comprise an annular ring with the support legs connected thereto. The holder assembly rests on the annular ring with the tissue valve suspended in the center of the ring. The invention can be used with stented or stentless valves

BRIEF DESCRIPTION OF THE DRAWINGS

FIG. 1 particularly illustrates how the various parts may be assembled.

FIG. 3A is a bottom view of a holder body for use in the tissue valve holder of the present invention.

FIG. 3B is a side view of the holder body illustrated in FIG. 3A.

FIG. 3C is a perspective view of the holder body illustrated in FIG. 3A.

FIGS. 7A and 7B are perspective views showing a handle and a holder body of FIG. 6.

FIG. 8 is an exploded view of a tissue valve holder in accordance with another embodiment of the present invention.

DETAILED DESCRIPTION OF THE PREFERRED EMBODIMENTS

The following detailed description of the invention should be read with reference to the drawings which are not necessarily to scale arid in which similar elements are numbered the same. The detailed description and drawings depict selected preferred embodiments and are not intended Lo limit the scope of the invention.

Figure 1:
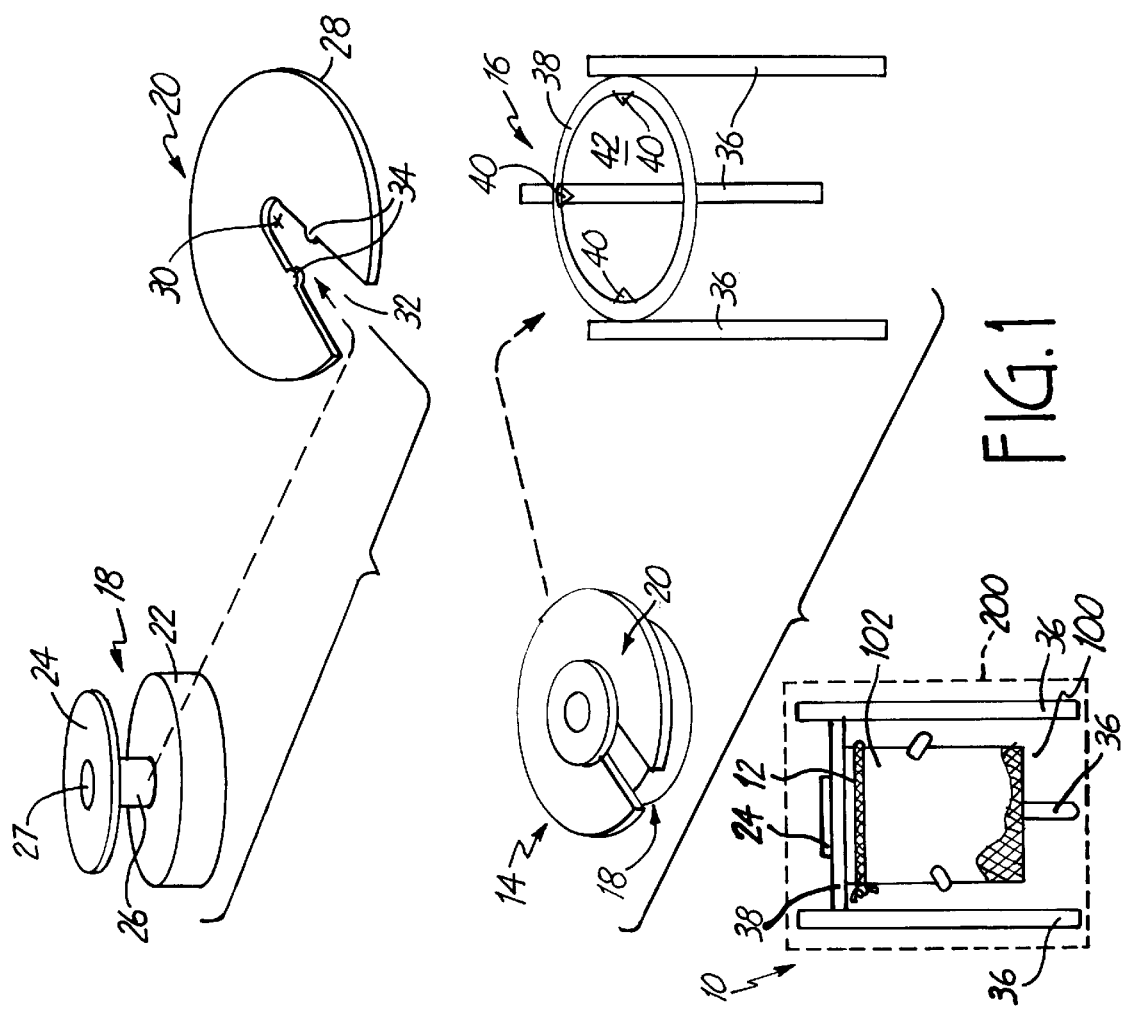
FIG. 1 is a perspective view of a tissue valve holder and associated parts in accordance with one embodiment of the present invention.

FIG. 1 illustrates a valve holder 10 for holding a valved conduit 100. A valved conduit refers to either a natural valved conduit, such as an aortic root, or a manufactured valved conduit which may be constructed from a combination of materials, such as a pericardial or synthetic conduit joined with either pericardial, synthetic, bioresorbable or porcine valve leaflets. Tissue valve holder 10 includes two primary components, namely, a holder assembly 14 and a support structure 16. The holder assembly 14 may include a holder body 18 and a removable disk 20. Although illustrated as two separate components, holder assembly 14 may comprise an integral one piece construction without departing from the scope and spirit of the present invention.

Figure 2:
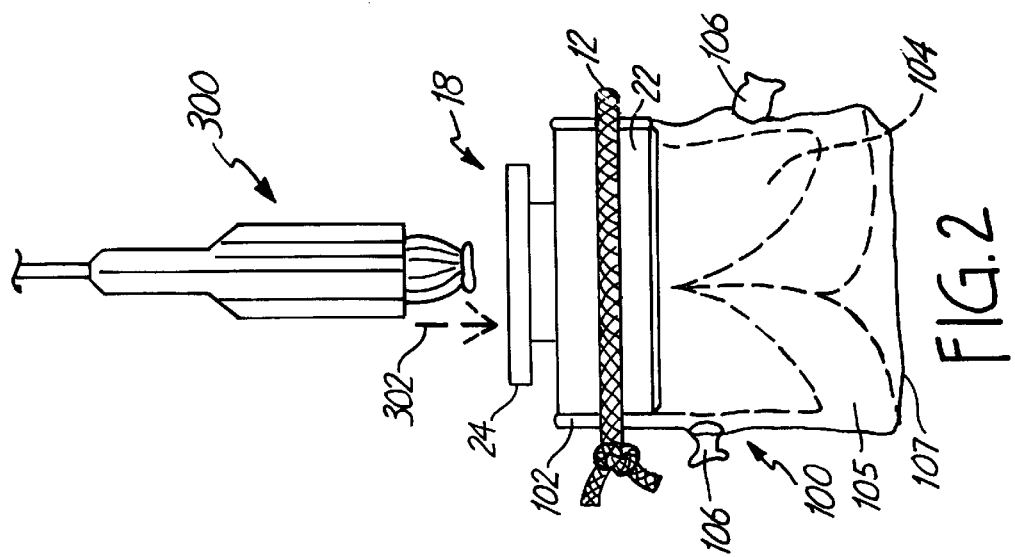
FIG. 2 is a side view of the tissue valve holder of FIG. 1 of the present invention and a handle for use therewith.

Holder body 18 includes a base portion 22 and a cap portion 24. A neck portion 26 extends between the base portion 22 and the cap portion 24. Additionally, neck 26 may be round or slightly squared to limit rotational movement. Holder body 18 further includes a keyed hole 27 extending through the cap portion 24, the neck portion 26 and the base portion 22 to receive a handle 300 as illustrated in FIG. 2.

Base portion 22 is adapted to fit in the conduit outflow 102 of the tissue valve or valved conduit 100. The holder body 18 may be secured to the tissue valve 100 by inserting the base portion 22 into the conduit outflow 102 and then tying a tape or cord 12 around the outside of the conduit outflow 102, to securely position but not damage valve 100, and not cause any tears in the valve 100. The tape or cord 12 may be made of a polymer fabric, suture or thread, such as polyester polyamide or polyterefluoroethylene (PTFE) or other suitable materials, such as elastic, rubber bands, or bioprosthetic materials, such as pericardium. Those skilled in the art will recognize that other means may be utilized to secure the conduit outflow 102 of the valve 100 to the base portion 22 of the holder body 18.

The base portion 22 of the holder body 18 may be generally cylindrical, having a continuous periphery such that a continuous interface is formed between the base portion 22 and the conduit outflow 102 of the tissue valve 100. By providing a continuous interface, the base portion 22 prevents deformation and/or damage to the tissue valve 100 during shipping and handling.

Disk 20 includes a periphery 28 and a center 30. A main slot 32 extends from the periphery 28 to the center 30 of the disk 20. The main slot 32 is sized to accommodate the neck portion 26 of the holder body 18. One or more protrusions 34 may be disposed along the inside edge of the main slot 32. The protrusions 34 are one way to establish an interference fit with the neck portion 26 of the holder body 18, although other mechanisms or configurations for protrusions 34 could be utilized. In this manner, the neck portion 26 of the holder body 18 may be inserted into the main slot 32 and advanced towards the center 30 of the disk 20. When the neck portion 26 engages the protrusions 34, additional force is required to advance the neck portion 26 to the center 30 of the disk 20. With this additional force, the neck portion 26 snaps into the center 30 of the disk 20 such that the protrusions 34 retain the neck portion 26 within slot 32 and thus the holder body 18 in the center 30 of the disk 20.

With the disk 20 positioned between the base portion 22 and the cap portion 24 of the holder body 18 such that the neck portion 26 is positioned in the main slot 32 of disk 20 adjacent the center 30, the holder assembly 14 may be placed on the support structure 16. Support structure 16 may include a plurality of support legs 36 connected to an annular ring 38. Three support legs 36 may be utilized, but those skilled in the art will recognize that more or less than three support legs 36 may be utilized. Structure 16 can be any desired shape, such as a continuous cylinder.

Annular ring 38 may optionally include protrusions 40 extending towards the center of the opening 42. The protrusions 40 are sized to provide a support surface or ledge on which the disk 20 rests. If the protrusions 40 are not utilized, the annular ring 38 provides a support on which the disk 20 rests. With this arrangement, the holder body 18 and tissue valve 100 secured thereto are suspended in the open portion 42 of the annular ring 38. The tissue valve holder 10 with the tissue valve 100 secured thereto may be placed in a suitable container 200 and sealed by conventional means. The container 200 may contain a suitable storage solution, such as ethanol, glutaraldehyde, formaldehyde, or saline, to preserve the valve 100 until it is ready for implantation by a surgeon.

By suspending the tissue valve 100, the holder 10 prevents undesirable contact with other surfaces, including container 200, regardless of whether the valve 100 remains in the container 200 or rests on another surface after removal from the container.

The holder body 18, the disk 20 and the support structure 16 may be made of polymer, such as a polysulfone, a polyacetyl or polyamide or other suitable biocompatable material capable of being sterilized. The holder body 18, the disk 20 and the support structure 16 may be made by injection molding, machined or other suitable manufacturing process.

The tissue valve holder of the present invention provides a number of advantages over prior art designs. For example, the tissue valve holder allows the tissue valve to remain suspended without contacting other surfaces regardless of whether or not the tissue valve holder and the tissue valve are in the container. This allows the valve to be sterilized without touching the container wall. Further, the tissue valve holder permits more consistent radiation dosage levels during sterilization because the valve is positioned in the same place in the container every time. In addition, the tissue valve holder provides better support to the tissue valve, and in particular, the conduit outflow to reduce the likelihood of deformation and/or damage during shipping and handling.

The tissue valve holder also allows the surgeon to more quickly implant the valve, thus reducing patient cross-clamp time because the valved conduit is pre-positioned on a holder. This eliminates the need to manually manipulate the device in order to position the device for implant. Furthermore, the tissue valve holder is easier to attach to the valve and easier to insert into the container.

FIG. 2 illustrates a side view of the holder body 18 and a handle 300 for use with the tissue valve holder 10. For purposes of illustration only, the support structure 16 and the disk 20 have been omitted for sake of clarity. Handle 300 may be inserted into keyed hole 27 of the holder body 18 as indicated by arrow 302. Handle 300 may be locked or unlocked simply by rotating the handle 300 in the keyed hole 27, or may be snap fit or threaded into hole 27. The details of the keyed hole 27 are illustrated by hidden lines as best seen in FIG. 3C. Handle 300 may be used to position and rotate the valve 100 into the desired position in the patient's heart.

As discussed previously, the tissue valve 100 is secured to the holder body 18 by inserting the base portion 22 into the conduit outflow 102 and securing tape or cord 12 to the outside of the conduit outflow 102. The base portion 22 is secured to the conduit outflow 102 above the leaflets 105 and the coronary arteries 106. Base portion 22 may form a continuous interface with the inside surface of the conduit outflow 102 in order to maintain the shape of the valve 100.

FIGS. 3A, 3B and 3C illustrate various detailed views of the holder body 18. Specifically, FIG. 3A is a bottom view, FIG. 3B is a side view and FIG. 3C is an isometric view of the holder body 18. Holder body 18 includes a base portion 22, a cap portion 24 and a neck portion 26 connected therebetween. Cap portion 24 has an outside diameter larger than the width of the main slot 32 of the disk 20, such that the cap portion 24 rests on the disk 20. Base portion 22 may include a recess or cavity 21 to form an annular ridge 29. The annular ridge 29 of the base portion 22 preferably forms a continuous interface with the conduit outflow 102 attached thereto Holder body 18 further includes a keyed hole 27 to receive a handle 300 as illustrated in FIG. 2. Keyed hole 27 includes a pair of through slots 25 and a pair of dead end slots 23. The handle is placed into slots 25 and rotated Into slots 23. The internal details of the keyed hole 27 are shown by hidden lines in FIG. 3C.

Figure 4C:
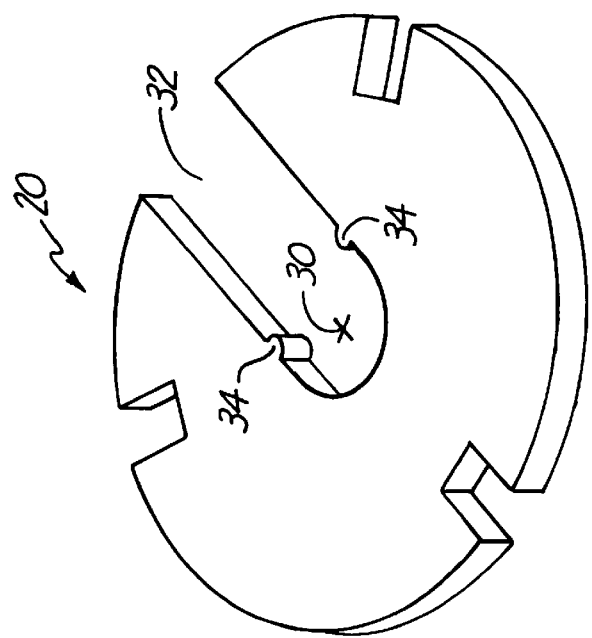
FIG. 4C is a perspective view of the disk illustrated in FIG. 4A.
Figure 4A:
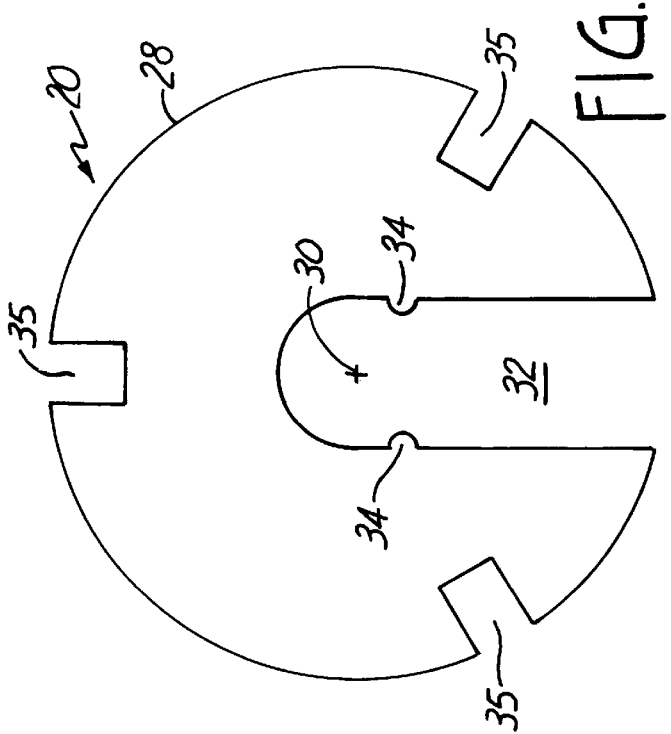
FIG. 4A is a top view of a disk for use in the tissue valve holder of the present invention.
Figure 4B:
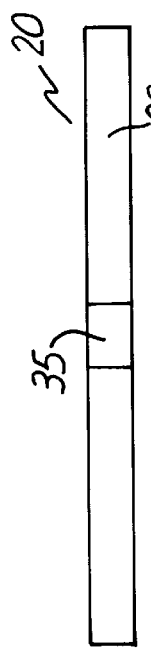
FIG. 4B is a side view of the disk illustrated in FIG. 4A.
Figure 5C:
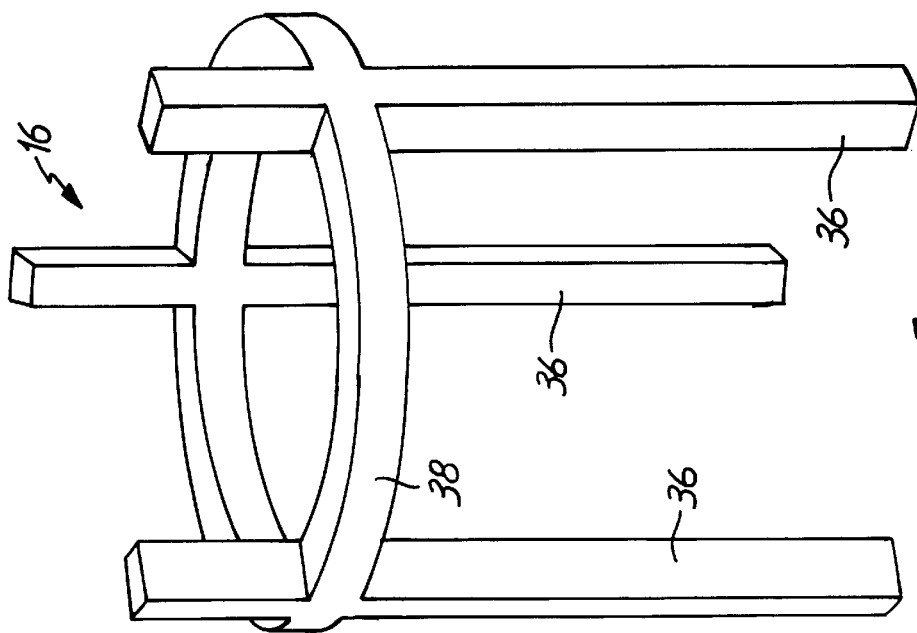
FIG. 5C is a perspective view of the support structure illustrated in FIG. 5A.
Figure 5B:
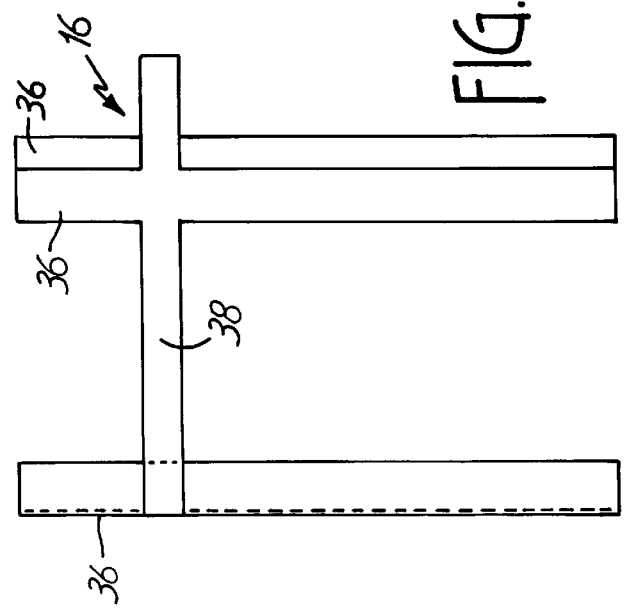
FIG. 5B is a top view of the support structure illustrated in FIG. 5A.
Figure 5A:
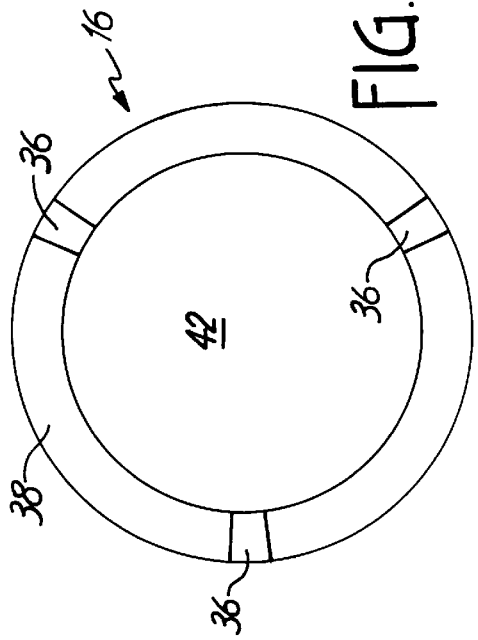
FIG. 5A is a side view of a support structure for use in the tissue valve holder of the present invention shown in FIG. 1.

FIGS. 4A, 4B and 4C illustrates various detailed views of the disk 20 for use in the tissue valve holder 10 of the present invention. FIG. 4A is a top view, FIG. 4B is a side view and FIG. 4C is a perspective view of the disk 20. Disk 20 includes a periphery 28 and a center 30. A plurality of slots 35 are provided to accommodate the portion of the support legs 36 that extend above the annular ring 38 as shown in FIGS. 5A–5C. The number of slots 35 may be varied to correspond to the number of support legs 36. Slots 35 may be omitted if the support legs 36 are attached to the periphery legs which may be integral with the annular ring 38 or if the protrusions 40 are used as the support surface. Legs 36 can also be flush with ring 38, so that slots 35 may be omitted.

In the embodiment of FIGS. 4A,B,C, disk 20 has an outside diameter that is larger than the inside diameter of the annular ring 38 of the support structure 16 to permit the disk 20 to rest on and be supported on the annular ring 38. If the protrusions 40 are used, the outside diameter of the disk 20 may be smaller than the inside diameter of the annular ring 38 but larger than the inside diameter of the protrusions 40 to permit the disk 20 to rest on and be supported by the protrusions 40.

FIGS. 5A, 5B and 5C illustrate various detailed views of the support structure 16 for use with the tissue valve holder 10 of the present invention. Specifically, FIG. 5A is a side view, FIG. 5B is a top view and FIG. 5C is a perspective view of the support structure 16. Support structure 16 includes a plurality of support legs 36 attached to the annular ring 38. The outside diameter of annular rind 38 .is sized to keep the valve 100 radially centered in the container 200. The support legs 36 may extend partially above the annular ring 38 and extend partially below the annular ring 38 to keep the tissue valve 100 vertically centered in the container 200. Support legs 36 extend below the annular ring 38 a sufficient distance to keep the tissue valve from touching any surface once removed from the container 200. In general, the legs can be integral with ring 38 circumference, can be positioned outside of ring 38, may be flush with top of ring 38, or can extend beyond ring 38.

Protrusion members 40 as illustrated in FIG. 1 may be used to provide a support surface for the disk 20 to rest on. If no protrusions 40 are utilized, as illustrated in FIGS. 5A–5C, the annular ring 38 provides a support surface for the disk 20 to rest on. With the holder body 18 secured in the main slot 32 of the disk 20, the holder assembly 14 and the tissue valve 100 secured thereto may be placed in the opening 42 of the support structure 16 with the disk 20 resting on the support surface 38 or 40 without contacting structure 16. In this position, the separate support structure 16 enables the holder 10 to suspend the tissue valve 100 without contacting any surface, whether or not the valve 100 is in a container 200 or on another surface after removal from the container 200.

To utilize this invention for valved conduit 100, the health professional opens contrarily 200. Handle 300 is inserted into keyed hole 27 of holder assembly 18. Holder assembly 18 is lifted and removed from container 200. Preferably, support structure 16 remains in container 200. Disk 20 is removed from holder assembly 18, making valved conduit 100 ready for implant. The health professional then sutures the inflow edge 107 of valved conduit 100 to the valve annulus of the patient. Then, cord 12 around valved conduit 100 is released or cut, releasing valved conduit 100 from holder assembly 18. Holder assembly 18 is then withdrawn. The conduit outflow 102 of the valved conduit 100 is sutured into position.

Figure 6:
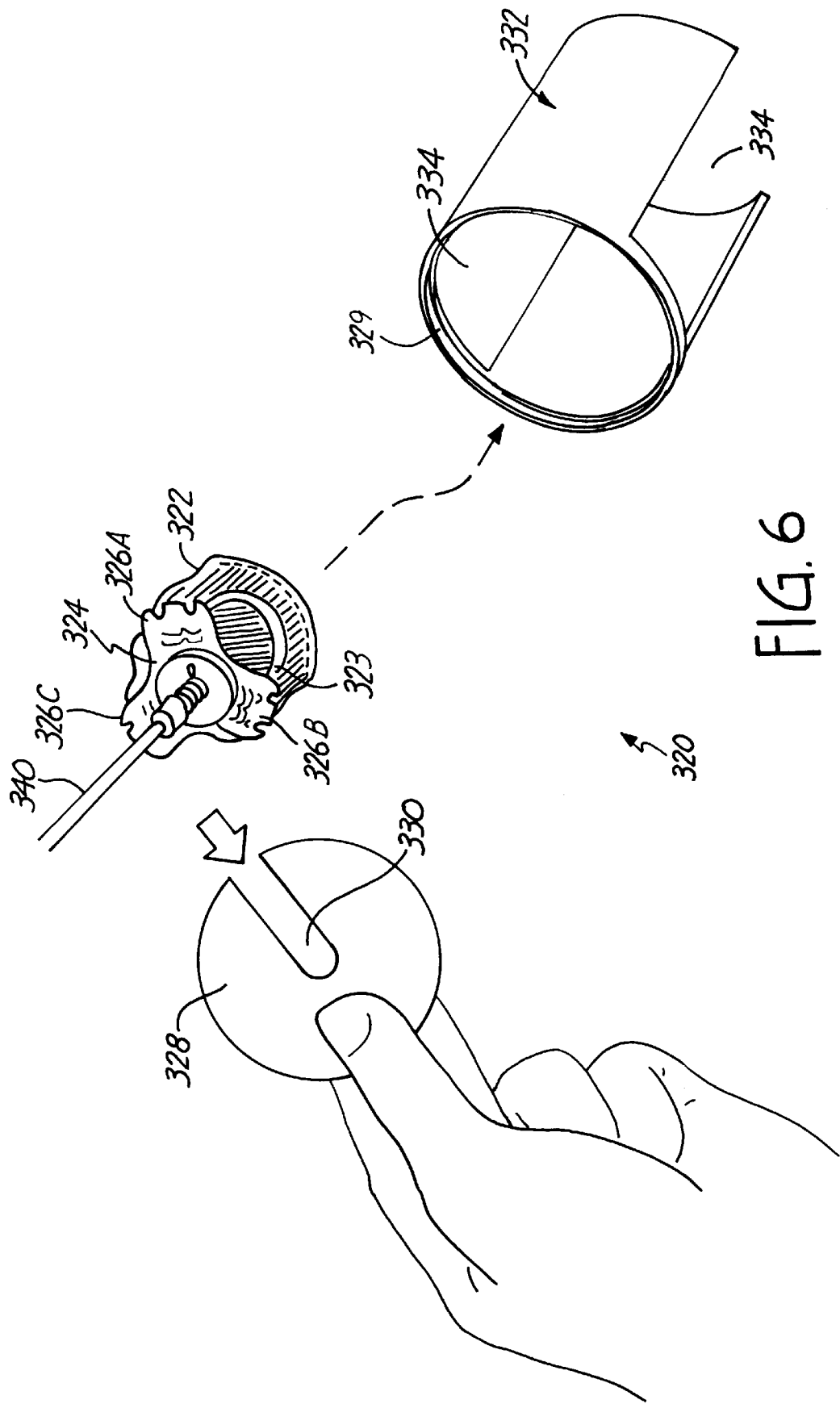
FIG. 6 is an exploded view of a tissue valve holder in accordance with another embodiment.

FIG. 6 is an exploded perspective view of a tissue valve holder 320 in accordance with another embodiment. Tissue valve holder 320 is adapted to hold a subcoronary stentless tissue valve 322 which is carried on a holder body 324. Holder body 324 has three arms 326A, 326B and 326C which are sutured to the commissure posts 323 of valve 322. Removable disk 328 includes slot 330 formed therein which is adapted to mate with holder body 324. Alternatively, the disks set forth in any of the embodiments herein can be hinged, collapsible or expandable. Valve 322 is suspended in support structure 332 which is generally cylindrical in shape and has two side openings 334 formed therein. Holder body 324 has a key hole formed therein adapted to receive a keyed handle 340 similar to that shown and described in U.S. Pat. No. 5,843,177. Other attachment techniques in any of the embodiments herein can also be used, such as a snap fit, a threaded coupling, or a friction fit. Disk 328 rests within recess of lip 329 or on top surface of support structure 332 which can then be placed in a container, as illustrated in FIG. 1.

FIGS. 7A and 7B show coupling of handle 340 to holder body 324. As illustrated in FIG. 7A, distal tip 342 of handle 340 is inserted into keyed slot 344. Once inserted, handle 340 is rotated relative to holder body 324 as illustrated in FIG. 7B thereby locking key tabs 346 in holder body 324. A spring 348 provides a separation force between handle 340 and holder body 324. Holder body 324 includes a neck (not shown) similar to neck 26 shown in FIG. 1 for receiving disk 328. FIGS. 7A and 7B also show scalpel guides 350. Sutures (not shown) are used to secure valve 322 to holder body 324. Sutures run through holes 352 adjacent scalpel guides 350 having a notch which is aligned with the suture, such that a scalpel may be run through the notch, thereby severing the suture and releasing valve 322 from holder body 324.

FIG. 8 is an exploded view of a tissue valve holder 348 in accordance with another embodiment for holding stented tissue valves, either mitral or aortic valves 353. A holder 355 is sutured onto the inflow edge of a mitral valve or the commissure posts of an aortic valve 353 and includes a threaded opening 354 formed therein. A holder support 356 includes a threaded screw 358 which is received in threaded opening 354. Holder support 356 includes radial extensions 360 each carrying protruding legs 362. Legs 362 abut the outer perimeter of valve 353 when holder support 356 is screwed into holder 355. A snap fit or friction fit can also be used. Holder support 356 fits into support structure 332 such that valve 353 is supported therein. Holder 356 rests on or in the recess of lip 329 of support structure 332 or top edge of support structure 332 and can be positioned in a container 200 as illustrated in FIG. 1. In this embodiment, the container is opened and tissue valve holder 348 is removed from container 200. Holder support 356 is threaded off of holder 355, and a handle is threaded in. Valve 353 is sutured into place. Sutures connecting valve 353 to holder 355 are cut, leaving the valve in place, and handle and holder 355 are removed.

Although the preceding detailed description sets forth selected preferred embodiments, those skilled in the art will appreciate the scope and spirit of the invention with reference to the appended claims. For example, any number of legs 36 can be used. Further, the holder may be used with any combination of configurations.

What is claimed is:

1. A holder and heart valve assembly, comprising:
   a tissue heart valve prosthesis which includes commissure posts;
   a holder assembly having a plurality of arms adapted to fit with the commissure posts;
   a suture coupling at least one of the arms to the commissure post to secure the commissure post to the arm;
   a support structure comprising a ring which extends around the prosthesis proximate the commissure posts and the arms of the holder assembly, the support structure having a plurality of support legs and a support surface formed in the ring, the legs extending from the ring, wherein the holder assembly fits with the support structure such that the tissue heart valve prosthesis is suspended from the holder assembly without contacting any other surface.

2. The holder and heart valve assembly of claim 1 including a removable disk adapted to couple to the holder assembly, wherein the removable disk rests on the support surface of the support structure.

3. The holder and heart valve assembly of claim 2 wherein the removable disk includes a slot formed therein adapted to engage the holder assembly.

4. The holder and heart valve assembly of claim 1 wherein the support structure includes two side openings formed therein.

5. The holder and heart valve assembly of claim 1 wherein the holder assembly includes suture holes and the holder assembly is sutured to the tissue heart valve prosthesis.

6. The holder and heart valve assembly of claim 5 wherein the holder assembly includes a scalpel guide having a notch formed therein adapted to guide a scalpel when cutting the suture.

7. The holder and heart valve assembly of claim 1 wherein the holder assembly is adapted to fit in a container and includes a keyed slot formed therein adapted to receive a tip of a handle having key tabs formed therein.

8. The holder and heart valve assembly of claim 1 wherein the holder assembly is adapted for coupling to a tissue heart valve prosthesis in either a mitral or aortic configuration.

9. The holder and heart valve assembly of claim 1 including a holder support adapted to couple to the holder assembly and wherein the holder support couples to the support structure.

10. The holder and heart valve assembly of A holder for holding a tissue heart valve prosthesis as in claim 9 wherein the holder support includes a threaded screw which is received in a threaded opening in the holder assembly.

11. A holder for holding a tissue heart valve prosthesis as in claim 9 wherein the holder support includes protruding legs adapted to abut an outer perimeter of the valve prosthesis.

* * * * *

UNITED STATES PATENT AND TRADEMARK OFFICE
CERTIFICATE OF CORRECTION

PATENT NO.    : 6,126,007
DATED         : October 3, 2000
INVENTOR(S)   : Erik E. Kari et al.

It is certified that error appears in the above-identified patent and that said Letters Patent is hereby corrected as shown below:

Col. 8, lines 19-20, delete "A holder for holding a tissue heart valve prosthesis as in".

Col. 8, lines 23-24, change "A holder for holding a tissue heart valve prosthesis as in" to --The Holder and heart valve assembly of--.

Signed and Sealed this

Eighth Day of May, 2001

Attest:

NICHOLAS P. GODICI

Attesting Officer    Acting Director of the United States Patent and Trademark Office